(12) United States Patent
Masopust, Jr. et al.

(10) Patent No.: US 12,370,256 B2
(45) Date of Patent: *Jul. 29, 2025

(54) ACTIVATION OF RESIDENT MEMORY T CELLS FOR THE TREATMENT OF CANCER

(71) Applicant: Regents of the University of Minnesota, Minneapolis, MN (US)

(72) Inventors: David B. Masopust, Jr., Minneapolis, MN (US); Vaiva D. Vezys, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/635,205

(22) PCT Filed: Aug. 3, 2018

(86) PCT No.: PCT/US2018/045244
§ 371 (c)(1),
(2) Date: Jan. 30, 2020

(87) PCT Pub. No.: WO2019/028406
PCT Pub. Date: Feb. 7, 2019

(65) Prior Publication Data
US 2021/0093713 A1    Apr. 1, 2021

Related U.S. Application Data

(60) Provisional application No. 62/540,831, filed on Aug. 3, 2017.

(51) Int. Cl.
| | | |
|---|---|---|
| A61K 39/39 | (2006.01) | |
| A61K 39/00 | (2006.01) | |
| A61K 39/145 | (2006.01) | |
| A61K 39/245 | (2006.01) | |
| A61K 39/395 | (2006.01) | |
| A61K 40/11 | (2025.01) | |
| A61K 40/31 | (2025.01) | |
| A61K 40/42 | (2025.01) | |
| A61K 40/46 | (2025.01) | |
| A61P 35/00 | (2006.01) | |
| C07K 16/28 | (2006.01) | |

(52) U.S. Cl.
CPC .......... *A61K 39/39* (2013.01); *A61K 39/0011* (2013.01); *A61K 39/145* (2013.01); *A61K 39/245* (2013.01); *A61K 39/39541* (2013.01); *A61K 40/11* (2025.01); *A61K 40/31* (2025.01); *A61K 40/4211* (2025.01); *A61K 40/46* (2025.01); *A61P 35/00* (2018.01); *C07K 16/2827* (2013.01); *A61K 2039/505* (2013.01); *A61K 2039/54* (2013.01); *A61K 2039/545* (2013.01); *A61K 2039/57* (2013.01); *A61K 2039/585* (2013.01); *A61K 2239/31* (2023.05); *A61K 2239/38* (2023.05); *A61K 2239/57* (2023.05); *C07K 2317/76* (2013.01)

(58) Field of Classification Search
CPC .... A61K 39/39; A61K 39/145; A61K 39/245; A61K 39/39541; A61K 2039/505; A61K 2039/54; A61K 2039/545; A61K 2039/57; A61K 2039/585; A61K 2039/5156; A61K 2039/5158; A61K 39/0011; A61K 2039/5252; A61P 35/00; C07K 16/2827; C07K 2317/76; C07K 14/7051; C07K 2319/03; Y02A 50/30
See application file for complete search history.

(56) References Cited

U.S. PATENT DOCUMENTS

| | | | |
|---|---|---|---|
| 9,950,056 B2 * | 4/2018 | Sampson | ........... A61K 39/4622 |
| 10,722,537 B2 * | 7/2020 | Masopust, Jr. | ......... A61P 35/00 |
| 11,642,401 B2 | 5/2023 | Masopust, Jr. et al. | |
| 2005/0019344 A1 | 1/2005 | Khanna et al. | |
| 2006/0120995 A1 | 6/2006 | Shah | |
| 2008/0107620 A1 | 5/2008 | Khanna | |
| 2009/0130144 A1 * | 5/2009 | Strome | ................ A61K 39/145 |
| | | | 424/246.1 |
| 2009/0304679 A1 * | 12/2009 | Weidanz | ............ C07K 14/7051 |
| | | | 424/130.1 |
| 2012/0020998 A1 | 1/2012 | Plumas et al. | |
| 2015/0366991 A1 * | 12/2015 | Schneck | ............ C07K 16/2833 |
| | | | 530/391.1 |
| 2016/0199479 A1 | 7/2016 | Su et al. | |
| 2016/0220665 A1 * | 8/2016 | Cobbold | .............. A61K 47/646 |

(Continued)

FOREIGN PATENT DOCUMENTS

| | | | | |
|---|---|---|---|---|
| WO | WO-03000720 A1 * | 1/2003 | ............. | A61P 31/12 |
| WO | WO 2012/123755 | 9/2012 | | |

(Continued)

OTHER PUBLICATIONS

Fujita Y, Taguchi H. Current status of multiple antigen-presenting peptide vaccine systems: Application of organic and inorganic nanoparticles. Chem Cent J. 2011;5(1):48. Published Aug. 23, 2011. doi:10.1186/1752-153X-5-48 (Year: 2011).*

Sawada Y, Yoshikawa T, Shimomura M, Iwama T, Endo I and Nakatsura T: Programmed death-1 blockade enhances the antitumor effects of peptide vaccine-induced peptide-specific cytotoxic T lymphocytes. Int J Oncol 46: 28-36, 2015 (Year: 2014).*

Von Eichborn, J., Woelke, A.L., Castiglione, F. et al. VaccImm: simulating peptide vaccination in cancer therapy. BMC Bioinformatics 14, 127 (2013). https://doi.org/10.1186/1471-2105-14-127 (Year: 2013).*

(Continued)

*Primary Examiner* — Meera Natarajan
*Assistant Examiner* — Francesca Edgingtongiordano
(74) *Attorney, Agent, or Firm* — Fish & Richardson P.C.

(57) ABSTRACT

Provided herein are improved methods of treating cancer in humans by activating resident memory T cells in tumors using one or more antigenic peptides.

13 Claims, 10 Drawing Sheets
Specification includes a Sequence Listing.

(56) References Cited

U.S. PATENT DOCUMENTS

| | | | |
|---|---|---|---|
| 2018/0325952 A1 | | 11/2018 | Masopust, Jr. et al. |
| 2021/0000935 A1* | | 1/2021 | Masopust, Jr. ........ A61K 35/17 |

FOREIGN PATENT DOCUMENTS

| | | | |
|---|---|---|---|
| WO | WO-2014140884 A2 * | 9/2014 | ............ A61K 35/14 |
| WO | WO 2015/069770 | 5/2015 | |
| WO | WO 2015/123496 | 8/2015 | |
| WO | WO-2015123496 A1 * | 8/2015 | ......... A61K 39/0011 |
| WO | WO 2017/079747 | 5/2017 | |
| WO | WO 2017/112830 | 6/2017 | |
| WO | WO 2017/177204 | 10/2017 | |

OTHER PUBLICATIONS

Lanitis E, Irving M, Coukos G. Targeting the tumor vasculature to enhance T cell activity. Curr Opin Immunol. Apr. 2015;33:55-63. doi: 10.1016/j.coi.2015.01.011. Epub Feb. 6, 2015. PMID: 25665467; PMCID: PMC4896929. (Year: 2015).*

EP Extended Search Report in European Appln. No. 18841686.1, dated Jul. 7, 2021, 8 pages.

Beckhove et al., "Specifically activated memory T cell subsets from cancer patients recognize and reject xenotransplanted autologous tumors," J. Clin. Invest., 114(1):67-76, Jul. 2004.

Casey et al., "Antigen-independent differentiation and maintenance of effector-like resident memory T cells in tissues," J. Immunol., 188(10):4866-75, May 2012.

Davies et al., "Capturing complex tumour biology in vitro: histological and molecular characterisation of precision cut slices," Sci. Reports, Dec. 9, 2015, 5:17187, 17 pages.

Erkes et al., "Virus-Specific CD8+ T Cells Infiltrate Melanoma Lesions and Retain Function Independently of PD-1 Expression," J. Immnol., 198:2979-2988, Feb. 2017.

Kim et al., "HISAT: a fast spliced aligner with low memory requirements," Nat. Methods, 12(4):357-60, Apr. 2015.

Kohlhapp et al., "NK cells and CD8+ T cells cooperate to improve therapeutic responses in melanoma treated with interleukin-2 (IL-2) and CTLA-4 blockade," J. Immunother., 3(18):1-13, May 2015.

LabCorp.com [online], "Patient Test Information: HLA Testing," available no later than Aug. 3, 2017, retrieved on Aug. 31, 2020, retrieved from URL<labcorp.com/help/patient-test-info/hla-testing>, 7 pages.

Love et al., "Moderated estimation of fold change and dispersion for RNA-seq data with DESeq2," Genome Biol., 15:550, Dec. 2014.

Masopust et al., "Dynamic T cell migration program provides resident memory within intestinal epithelium," J. Exp. Med., 207(3):553-64, Mar. 2010.

Millar et al., "Antibody-mediated delivery of viral epitopes to tumors harnesses CMV-specific T cells for cancer therapy," Nature Biotechnology, Feb. 2020, 38(4):420-425.

Nishio et al., "Armed oncolytic virus enhances immune functions of chimeric antigen receptor—modified T cells in solid tumors," cancer research, 74(18):5195-205, Jul. 2014.

Pauken et al., "Cutting edge: identification of autoreactive CD4+ and CD8+ T cell subsets resistant to PD-1 pathway blockade," J. Immunol., 194(8):3551-3555, Apr. 2015.

PCT International Preliminary Report on Patentabilty in International Appln. No. PCT/US2016/060834, dated May 8, 2018, 6 pages.

PCT International Preliminary Report on Patentabilty in International Appln. No. PCT/US2018/045244; dated Mar. 10, 2020, 10 pages.

PCT International Search Report and Written Opinion in International Appln. No. PCT/US2016/060834 dated Jan. 24, 2017, 7 pages.

PCT International Search Report and Written Opinion in International Appln. No. PCT/US2018/045244, dated Dec. 21, 2018, 10 pages.

Schenkel et al., "Resident memory CD8 T cells trigger protective innate and adaptive immune responses," Science, 346(6205):98-101, Oct. 2014.

Schenkel et al., "Sensing and alarm function of resident memory $CD8^+T$ cells," Nat. Immunol., 14(5):509-14, May 2013.

Simoni et al., "Bystander CD8+ T cells are abundant and phenotypically distinct in human tumour infiltrates," Nat., 557:575-579, May 2018.

Steinert et al., "Quantifying memory CD8 T cells reveals regionalization of immunosurveillance," Cell, 161(4):737-49, May 2015.

Wang et al., "Manufacture of tumor-and virus-specific T lymphocytes for adoptive cell therapies," Cancer Gene Therapy, 22(2):85, Feb. 2015.

U.S. Appl. No. 15/774,163, filed May 7, 2018, David B. Masopust Jr., Issued.

U.S. Appl. No. 16/939,962, filed Jul. 27, 2020, David B. Masopust Jr., Published.

Cuburu et al., "Harnessing anti-cytomegalovirus immunity for local immunotherapy against solid tumors," Proc. Natl. Acad. Sci. USA, Jun. 2022, 119(26):e2116738119.

Kines et al., "An infrared dye-conjugated virus-like particle for the treatment of primary uveal melanoma," Mol. Cancer Ther., Feb. 2018, 17(2):565-574.

Ning et al., "Functional virus-specific memory T cells survey glioblastoma," Cancer Immunol. Immunother., Aug. 2022, 71(8):1863-1875.

Ravindran, "QnAs with John T. Schiller," Proc. Natl. Acad. Sci. USA, Jul. 2022, 119(31):e2209619119.

Rosato et al., "Virus-specific memory T cells populate tumors and can be repurposed for tumor immunotherapy," Nat. Commun., Feb. 2019, 10(1):567.

\* cited by examiner

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial
<220> FEATURE:
<223> OTHER INFORMATION: Synthetically generated peptide

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial
<220> FEATURE:
<223> OTHER INFORMATION: Synthetically generated peptide

<400> SEQUENCE: 2

Lys Ala Val Tyr Asn Phe Ala Thr Met
1               5

<210> SEQ ID NO 3
<211> LENGTH: 9
<212> TYPE: PRT
<213> ORGANISM: Artificial
<220> FEATURE:
<223> OTHER INFORMATION: Synthetically generated peptide

<400> SEQUENCE: 3

Gly Leu Cys Thr Leu Val Ala Met Leu
1               5

<210> SEQ ID NO 4
<211> LENGTH: 9
<212> TYPE: PRT
<213> ORGANISM: Artificial
<220> FEATURE:
```

```
<223> OTHER INFORMATION: Synthetically generated peptide

<400> SEQUENCE: 4

Cys Leu Gly Gly Leu Leu Thr Met Val
1               5

<210> SEQ ID NO 5
<211> LENGTH: 9
<212> TYPE: PRT
<213> ORGANISM: Artificial
<220> FEATURE:
<223> OTHER INFORMATION: Synthetically generated peptide

<400> SEQUENCE: 5

Asn Leu Val Pro Met Val Ala Thr Val
1               5

<210> SEQ ID NO 6
<211> LENGTH: 9
<212> TYPE: PRT
<213> ORGANISM: Artificial
<220> FEATURE:
<223> OTHER INFORMATION: Synthetically generated peptide

<400> SEQUENCE: 6

Gly Ile Leu Gly Phe Val Phe Thr Leu
1               5

<210> SEQ ID NO 7
<211> LENGTH: 9
<212> TYPE: PRT
<213> ORGANISM: Artificial
<220> FEATURE:
<223> OTHER INFORMATION: Synthetically generated peptide

<400> SEQUENCE: 7

Phe Arg Cys Pro Arg Arg Phe Cys Phe
1               5

<210> SEQ ID NO 8
<211> LENGTH: 9
<212> TYPE: PRT
<213> ORGANISM: Artificial
<220> FEATURE:
<223> OTHER INFORMATION: Synthetically generated peptide

<400> SEQUENCE: 8

Cys Arg Val Leu Cys Cys Tyr Val Leu
1               5

<210> SEQ ID NO 9
<211> LENGTH: 10
<212> TYPE: PRT
<213> ORGANISM: Artificial
<220> FEATURE:
<223> OTHER INFORMATION: Synthetically generated peptide

<400> SEQUENCE: 9

Asp Tyr Cys Asn Val Leu Asn Lys Glu Phe
1               5                   10

<210> SEQ ID NO 10
<211> LENGTH: 10
<212> TYPE: PRT
<213> ORGANISM: Artificial
<220> FEATURE:
<223> OTHER INFORMATION: Synthetically generated peptide
```

```
<400> SEQUENCE: 10

Leu Tyr Thr Ser Arg Met Val Thr Asn Leu
1               5                   10

<210> SEQ ID NO 11
<211> LENGTH: 10
<212> TYPE: PRT
<213> ORGANISM: Artificial
<220> FEATURE:
<223> OTHER INFORMATION: Synthetically generated peptide

<400> SEQUENCE: 11

Leu Tyr Pro Arg Pro Pro Gly Ser Gly Leu
1               5                   10

<210> SEQ ID NO 12
<211> LENGTH: 9
<212> TYPE: PRT
<213> ORGANISM: Artificial
<220> FEATURE:
<223> OTHER INFORMATION: Synthetically generated peptide

<400> SEQUENCE: 12

Gln Tyr Asp Pro Val Ala Ala Leu Phe
1               5

<210> SEQ ID NO 13
<211> LENGTH: 9
<212> TYPE: PRT
<213> ORGANISM: Artificial
<220> FEATURE:
<223> OTHER INFORMATION: Synthetically generated peptide

<400> SEQUENCE: 13

Val Thr Glu His Asp Thr Leu Leu Tyr
1               5

<210> SEQ ID NO 14
<211> LENGTH: 9
<212> TYPE: PRT
<213> ORGANISM: Artificial
<220> FEATURE:
<223> OTHER INFORMATION: Synthetically generated peptide

<400> SEQUENCE: 14

Arg Gly Asp Pro Phe Asp Lys Asn Tyr
1               5

<210> SEQ ID NO 15
<211> LENGTH: 9
<212> TYPE: PRT
<213> ORGANISM: Artificial
<220> FEATURE:
<223> OTHER INFORMATION: Synthetically generated peptide

<400> SEQUENCE: 15

Val Ser Asp Gly Gly Pro Asn Leu Tyr
1               5

<210> SEQ ID NO 16
<211> LENGTH: 9
<212> TYPE: PRT
<213> ORGANISM: Artificial
<220> FEATURE:
<223> OTHER INFORMATION: Synthetically generated peptide
```

```
<400> SEQUENCE: 16

Ile Val Thr Asp Phe Ser Val Ile Lys
1               5

<210> SEQ ID NO 17
<211> LENGTH: 9
<212> TYPE: PRT
<213> ORGANISM: Artificial
<220> FEATURE:
<223> OTHER INFORMATION: Synthetically generated peptide

<400> SEQUENCE: 17

Ala Thr Ile Gly Thr Ala Met Tyr Lys
1               5

<210> SEQ ID NO 18
<211> LENGTH: 9
<212> TYPE: PRT
<213> ORGANISM: Artificial
<220> FEATURE:
<223> OTHER INFORMATION: Synthetically generated peptide

<400> SEQUENCE: 18

Arg Pro Pro Ile Phe Ile Arg Arg Leu
1               5

<210> SEQ ID NO 19
<211> LENGTH: 9
<212> TYPE: PRT
<213> ORGANISM: Artificial
<220> FEATURE:
<223> OTHER INFORMATION: Synthetically generated peptide

<400> SEQUENCE: 19

Lys Ala Arg Asp His Leu Ala Val Leu
1               5

<210> SEQ ID NO 20
<211> LENGTH: 9
<212> TYPE: PRT
<213> ORGANISM: Artificial
<220> FEATURE:
<223> OTHER INFORMATION: Synthetically generated peptide

<400> SEQUENCE: 20

Asn Val Arg Arg Ser Trp Glu Glu Leu
1               5

<210> SEQ ID NO 21
<211> LENGTH: 10
<212> TYPE: PRT
<213> ORGANISM: Artificial
<220> FEATURE:
<223> OTHER INFORMATION: Synthetically generated peptide

<400> SEQUENCE: 21

Thr Pro Arg Val Thr Gly Gly Gly Ala Met
1               5                   10

<210> SEQ ID NO 22
<211> LENGTH: 9
<212> TYPE: PRT
<213> ORGANISM: Artificial
<220> FEATURE:
<223> OTHER INFORMATION: Synthetically generated peptide

<400> SEQUENCE: 22
```

```
Leu Pro Phe Asp Arg Thr Thr Val Met
1               5

<210> SEQ ID NO 23
<211> LENGTH: 9
<212> TYPE: PRT
<213> ORGANISM: Artificial
<220> FEATURE:
<223> OTHER INFORMATION: Synthetically generated peptide

<400> SEQUENCE: 23

Arg Val Arg Ala Tyr Thr Tyr Ser Lys
1               5

<210> SEQ ID NO 24
<211> LENGTH: 9
<212> TYPE: PRT
<213> ORGANISM: Artificial
<220> FEATURE:
<223> OTHER INFORMATION: Synthetically generated peptide

<400> SEQUENCE: 24

Thr Leu Leu Asn Cys Ala Val Thr Lys
1               5

<210> SEQ ID NO 25
<211> LENGTH: 9
<212> TYPE: PRT
<213> ORGANISM: Artificial
<220> FEATURE:
<223> OTHER INFORMATION: Synthetically generated peptide

<400> SEQUENCE: 25

Thr Val Arg Ser His Cys Val Ser Lys
1               5

<210> SEQ ID NO 26
<211> LENGTH: 9
<212> TYPE: PRT
<213> ORGANISM: Artificial
<220> FEATURE:
<223> OTHER INFORMATION: Synthetically generated peptide

<400> SEQUENCE: 26

Ile Leu Arg Gly Ser Val Ala His Lys
1               5
```

ACTIVATION OF RESIDENT MEMORY T CELLS FOR THE TREATMENT OF CANCER

CROSS-REFERENCE TO RELATED APPLICATIONS

This application is a National Stage application under 35 U.S.C. § 371 of International Application No. PCT/US2018/045244 having an International Filing Date of Aug. 3, 2018, which claims priority to U.S. Application Ser. No. 62/540,831, filed on Aug. 3, 2017. The disclosure of the prior applications are considered part of the disclosure of this application, and are incorporated in their entirety into this application.

TECHNICAL FIELD

This disclosure generally relates to immunology and, specifically, the activation of resident memory T cells.

BACKGROUND

Current data supports a model by which early effector CD8 T cells migrate throughout the body, differentiate into long-lived memory CD8 T cells, and maintain surveillance of non-lymphoid tissues. Methods are described herein whereby non-lymphoid memory T cells are reactivated and significantly improve the effects of immunotherapy.

SUMMARY

In one aspect, a method of treating a solid tumor in a human subject is provided. Such a method typically includes administering immunotherapy to the subject and administering a composition comprising at least one antigenic peptide to the solid tumor.

In some embodiments, the immunotherapy is selected from the group consisting of CAR T cells, monoclonal antibodies, checkpoint blockade inhibitors, and personalized vaccines.

In some embodiments, the at least one antigenic peptide is selected from the group consisting of the peptides shown in Table 1. In some embodiments, the composition includes at least two different antigenic peptides (e.g., at least five different antigenic peptides, at least ten different antigenic peptides, or at least twenty different antigenic peptides). In some embodiments, the composition comprises at least one antigenic peptide from a virus (e.g., an influenza virus, a cold virus, an adenovirus, an adeno-associated virus, a cytomegalovirus (CMV), a measles virus (e.g., rubeola), an Epstein-Barr virus, human papillomavirus (HPV), a norovirus, a polyoma virus, a hepatitis A, B and/or C virus, a Zika virus, a respiratory syncytial virus (RSV), or a herpes simplex virus (HSV)) or a bacteria (e.g., *Escherichia coli*, *Salmonella*, *Helicobacter pylori*, *Staphylococcus aureus*, *Streptococcal* spp., or *Campylobacter* spp.). In some embodiments, the composition includes at least one antigenic peptide from a vaccine (e.g., a chickenpox vaccine, a polio vaccine, a German measles vaccine, a mumps vaccine, a yellow fever vaccine, a smallpox vaccine, a Diphtheria vaccine, and a tetanus vaccine).

In some embodiments, the composition comprises at least two antigenic peptides from a first microorganism, at least two antigenic peptides from a second microorganism and at least two antigenic peptides from a third microorganism. In some embodiments, the composition comprises at least three antigenic peptides from a first microorganism, at least three antigenic peptides from a second microorganism and at least three antigenic peptides from a third microorganism. In some embodiments, the first microorganism is EBV, wherein the second microorganism is CMV, and wherein the third microorganism is influenza.

In some embodiments, the composition including at least one antigenic peptide is administered to the solid tumor via injection. In some embodiments, the composition comprising at least one antigenic peptide is administered to the solid tumor a plurality of times.

In some embodiments, the methods further include determining the major histocompatibility complex (MHC)/Human Leukocyte Antigen (HLA) genotype of the subject and using that information to determine the particular plurality of peptides that are administered.

In some embodiments, the methods further include monitoring at least one of the following or at least two of the following or at least three of the following: size of the solid tumor; presence and/or amount of one or more chemokines; presence and/or amount of leukocytes; presence and/or amount of serum antibodies; presence and/or amount of an immunotherapeutic associated with or in the vicinity of the solid tumor; activation of local dendritic cells; activation of NK cells; and/or up-regulation of vascular adhesion molecules.

In some embodiments, the solid tumor is selected from the group consisting of glioblastoma, colon cancer, melanoma, breast cancer, pancreatic cancer, head and neck cancer, and retinoblastoma.

In another aspect, an article of manufacture is provided that includes an immunotherapeutic composition and a composition comprising a plurality of antigenic peptides.

In some embodiments, the immunotherapeutic composition is selected from the group consisting of CAR T cells, a monoclonal antibody, and checkpoint blockade inhibitors.

In some embodiments, the plurality of antigenic peptides includes 4 to 6 different antigenic peptides. In some embodiments, the plurality of antigenic peptides includes peptides that are about 8 to about 10 amino acids in length. In some embodiments, the plurality of antigenic peptides includes about 100 to about 200 different antigenic peptides. In some embodiments, the plurality of antigenic peptides includes peptides that are about 20 amino acids in length. In some embodiments, the plurality of antigenic peptides are from a plurality of common pathogens.

In some embodiments, the article of manufacture is designed for a particular HLA genotype.

In one aspect, a method of treating a solid tumor in a subject is provided. Such a method typically includes administering a composition that includes at least one antigenic peptide to the solid tumor.

In some embodiments, the administering step includes injecting the composition into the solid tumor. In some embodiments, the administering step includes topically applying the composition to the solid tumor or to an area adjacent or near the solid tumor.

In some embodiments, the composition includes at least two different antigenic peptides. In some embodiments, the composition includes at least five different antigenic peptides. In some embodiments, the composition includes at least ten different antigenic peptides. In some embodiments, the composition includes at least twenty different antigenic peptides.

In some embodiments, the composition comprises at least one antigenic peptide from a virus or a bacteria. Representative viruses include, without limitation, an influenza virus, a cold virus, an adenovirus, an adeno-associated virus, a cytomegalovirus (CMV), a measles virus (e.g., rubeola), an Epstein-Barr virus, human papillomavirus (HPV), a norovirus, a polyoma virus, a hepatitis A, B and/or C virus, a Zika virus, a respiratory syncytial virus (RSV), or a herpes simplex virus (HSV). Representative bacteria include, without limitation, *Escherichia coli, Salmonella, Helicobacter pylori, Staphylococcus aureus, Streptococcal* spp., or *Campylobacter* spp.

In some embodiments, the composition includes at least one antigenic peptide from a vaccine. Representative vaccines include, without limitation, a chickenpox vaccine, a polio vaccine, a German measles vaccine, a mumps vaccine, a yellow fever vaccine, a smallpox vaccine, a Diphtheria vaccine, and a tetanus vaccine.

In some embodiments, the composition includes at least two antigenic peptides from a first microorganism, at least two antigenic peptides from a second microorganism and at least two antigenic peptides from a third microorganism. In some embodiments, the composition includes at least three antigenic peptides from a first microorganism, at least three antigenic peptides from a second microorganism and at least three antigenic peptides from a third microorganism. In some embodiments, the first microorganism is EBV, the second microorganism is CMV, and the third microorganism is influenza.

In some embodiments, the administration step is performed more than once. In some embodiments, the administration step is performed a plurality of times.

In some embodiments, the methods described herein further include determining the major histocompatibility complex (MHC) genotype of the subject. In some embodiments, the methods described herein further include monitoring at least one of the following or at least two of the following or at least three of the following: size of the solid tumor; presence and/or amount of one or more chemokines (e.g., CXCL9, CXCL10, fractalkine, CCL2, CCL3/4, CCLS); presence and/or amount of leukocytes (e.g., inflammatory monocytes, B cells); presence and/or amount of serum antibodies; presence and/or amount of a cancer immunotherapeutic (e.g., CAR-T cells) associated with or in the vicinity of the solid tumor; activation of local dendritic cells; activation of NK cells; and/or up-regulation of vascular adhesion molecules (e.g., VCAM-1).

In some embodiments, the methods described herein further include administering immunotherapy to the subject. Representative immunotherapy includes, without limitation, CAR T cells, a monoclonal antibody (e.g., Opdivo), checkpoint blockade inhibitors, and personalized vaccines.

In some embodiments, the solid tumor is glioblastoma, colon cancer, melanoma, breast cancer, pancreatic cancer, head and neck cancer, and retinoblastoma.

In another aspect, an article of manufacture is provided that includes a plurality of antigenic peptides. In some embodiments, the plurality of antigenic peptides comprises 4 to 6 different antigenic peptides. In some embodiments, the plurality of antigenic peptides comprises peptides that are about 8 to about 10 amino acids in length. In some embodiments, the plurality of antigenic peptides comprises about 100 to about 200 different antigenic peptides. In some embodiments, the plurality of antigenic peptides comprises peptides that are about 20 amino acids in length.

In some embodiments, the article of manufacture is designed for a particular HLA genotype. In some embodiments, the antigenic peptides are from a plurality of common pathogens.

In some embodiments, the article of manufacture further includes an immunotherapeutic composition. Representative immunotherapeutic composition include, without limitation, CAR T cells and checkpoint blockade inhibitors.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 5 shows that peptide alarm therapy synergizes with PD-L1 blockade.

DETAILED DESCRIPTION

Figure 1:
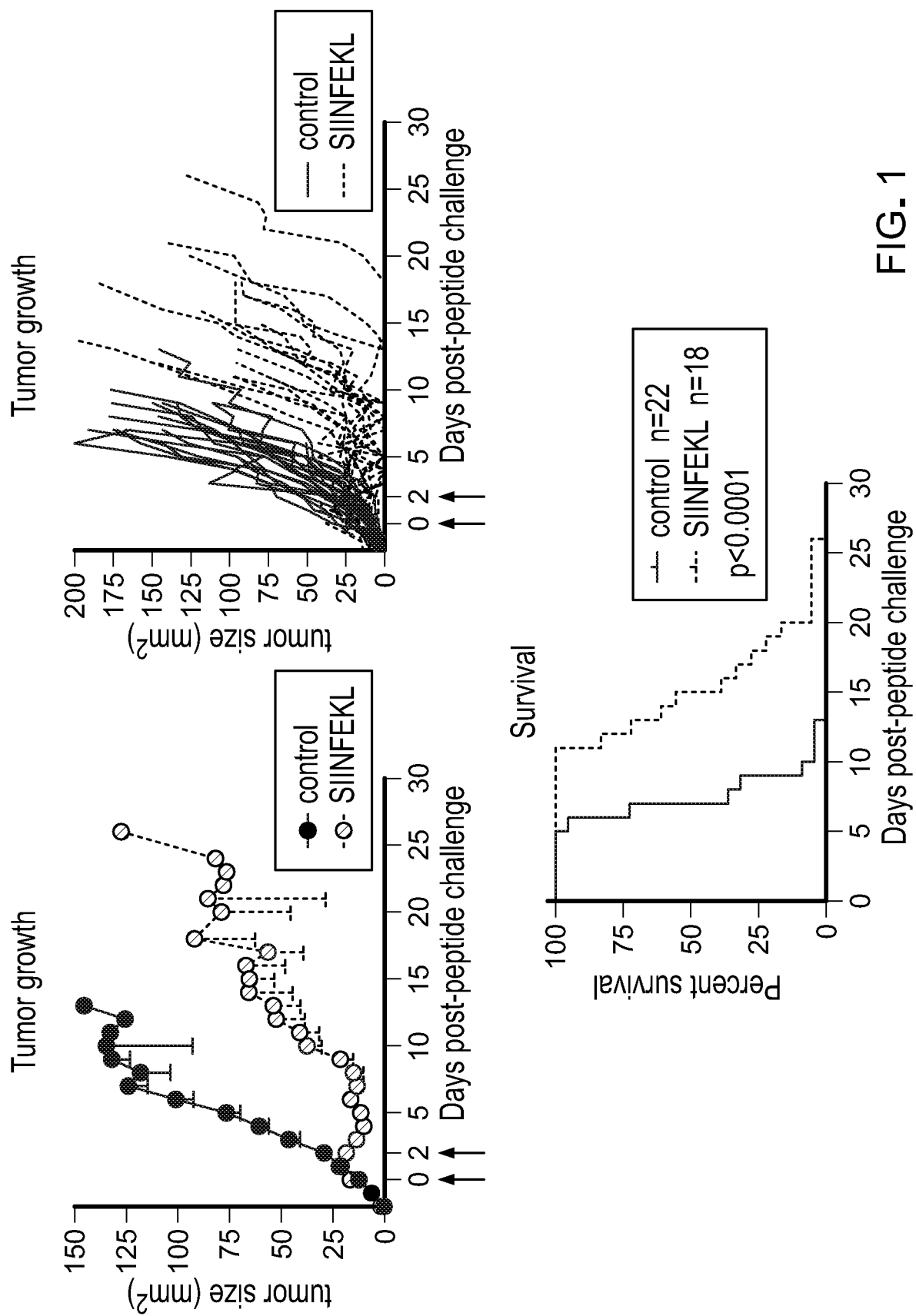
FIG. 1 is data showing adult C57B/6 mice that were given naïve OTI CD8 T cells, which are specific for the SIINFEKL (SEQ ID NO:1) peptide of chicken ovalbumin (ova). The next day, all animals were infected iv with a recombinant vesicular stomatitis virus producing chicken ovalbumin (VSV-ova). This induces memory OTI CD8 T cells. 32-45 days later, $1 \times 10^5$ B16 melanoma cells were injected subcutaneously. When tumors were palpable (day 7-10), 0.5 µg peptide in 30 µl PBS was injected into the tumor twice, 2 days apart. Tumor size was monitored with calipers. Panel A shows the average tumor size in mice injected with irrelevant (control) peptide (black) or injected with SIINFEKL (SEQ ID NO:1) peptide to stimulate OTI memory T cells (red). Panel B shows the same as Panel A, except each line is an individual animal. Panel C shows the mice surviving with irrelevant peptide injection (black line) and SIINFEKL (SEQ ID NO:1) peptide injection to stimulate OTI memory cells (red line), based on the same animals as in Panel A.

TRM refers to memory T cells that are present within non-lymphoid tissues regardless of recirculation properties. Microbe-specific $T_{RM}$ exist in every soft tissue throughout the body, and are established in response to human infections and vaccines that everyone has experienced. $T_{RM}$ can be reactivated locally by local injection of very specific, short peptides in the absence of any additional adjuvant, referred to herein as peptide alarm therapy, and, significantly, local $T_{RM}$ re-activation in tumors results in recruitment and activation of CD8 T cells and NK cells, activation of dendritic cells, and reduced tumor burden.

It has been shown that $T_{RM}$ reactivation via short peptides (i.e., peptide alarm therapy) can switch the tumor microenvironment from immune-suppressive to immune-stimulatory, thereby promoting tumor clearance. See, for example, WO 2017/079747. For example, many cells in the tumor exhibit immune-activated and/or immune-stimulatory phenotypes following injection of $T_{RM}$ reactivating peptide into tumors. Such immune-activated and immune-stimulatory phenotypes can include, without limitation, recruitment of CD8+ T cells to the tumor site; an increase (e.g., a 2-fold, 5-fold or 10-fold increase) in the concentration of natural killer cells within the tumor; activation of CD8+ T cells and natural killer cells as indicated by expression of interferon gamma and/or granzyme B; and activation of dendritic cells as indicated by upregulation of CD80/86, MHC II, CCR7, and an increased number of CD103+ dendritic cells in the draining lymph node.

This document takes that discovery even further by demonstrating that peptide alarm therapy in combination with immunotherapy is synergistic.

This document describes experiments that demonstrate that peptide alarm therapy significantly enhanced the recruitment of CART cells. Currently, CART cell therapy works well for "liquid" cancers, such as leukemia. Solid tumors, however, do not respond well to CAR T cell therapy, in part due to the inability of CAR T cells to focus migration to solid tumors. As demonstrated herein, however, the activation of microbe-specific memory CD8 T cells in tumors resulting from peptide alarm therapy significantly improves the recruitment of CAR T cells to solid tumors. It would be understood that solid tumors include, for example, glioblastoma, colon cancer, melanoma, breast cancer, pancreatic cancer, head and neck cancer, ovarian cancer, lung cancer, liver cancer, prostate cancer, kidney cancer, and retinoblastoma. As demonstrated herein, the activation of microbe-specific memory CD8 T cells in tumors resulting from peptide alarm therapy acts synergistically with PD-L1 blockade, which is an FDA-approved therapy for multiple cancers.

Based on the results described herein with PD-L1 blockade, it would be expected that other types of immunotherapies also would exhibit synergy with peptide alarm therapy. For example, other cancer immunotherapies include, without limitation, checkpoint blockade, monoclonal antibodies, CAR T cells, and personalized vaccines, each of which would be expected to exhibit synergy with peptide alarm therapy. Non-limiting examples of immunotherapy include, for example, CTLA4 checkpoint blockade therapy; checkpoint blockade therapy targeting other pathways; combinations of checkpoint blockade therapy (e.g., CTLA4 blockade and PD-1/PD-L1 blockade), oncolytic virus therapy (e.g., Imlygic®), STING antagonism therapy, the Opdivo® monoclonal antibody, the Keytruda® monoclonal antibody, the Tecentriq® monoclonal antibody, or combinations thereof.

Immunotherapy is known in the art. The regimen for administration has been established for existing immunotherapies and can be readily determined for new immunotherapies. Immunotherapies typically are administered intravenously, but can be administered using any suitable route.

Peptides are known in the art and generally refer to chains of amino acids linked by amide (or peptide) bonds. Peptides sometimes are defined as being less than about 50 amino acids in length (e.g., about 5 to about 50 amino acids, about 5 to about 45 amino acids, about 8 to about 45 amino acids, about 10 to about 40 amino acids, about 15 to about 35 amino acids, about 20 to about 30 amino acids, about 20 to about 50 amino acids, or about 25 to about 50 amino acids in length) but, as used herein, peptides also can be longer than 50 amino acids in length (e.g., up to about 55 amino acids, up to about 60 amino acids, up to about 70 amino acids, up to about 80 amino acids, up to about 90 amino acids, or up to about 100 amino acids). Peptides as used herein (e.g., antigenic peptides) generally contain naturally occurring amino acids, but can include non-naturally occurring amino acids to the extent that recognition of the antigenic peptide by T cells (e.g., Tri cells) is not impeded or disrupted.

As used herein, antigenic peptides are those peptides that, when administered to a tumor (e.g., a solid tumor), activate the resident memory T cells that reside therein. An antigenic peptide, also referred to as an immunogenic peptide, is understood in the art to refer to a peptide that produces, or results in, an antigen-specific stimulation of T cells. As used herein, an antigenic peptide is a peptide from any microorganism with which the subject has previously been infected and to which the subject has previously developed an immune response against. The infection can be a result of a previous infection or exposure via a vaccine. Simply by way of example, the source of an antigenic peptide can be, without limitation, a virus against which the subject has developed an immune response (e.g., an influenza virus, a cold virus, an adenovirus, an adeno-associated virus, a cytomegalovirus (CMV), a measles virus (e.g., rubeola), an Epstein-Barr virus (EBV), human papillomavirus (HPV), a norovirus, a polyoma virus, a hepatitis A, B and/or C virus, a Zika virus, a respiratory syncytial virus (RSV), or a herpes simplex virus (HSV)), a bacteria against which the subject has developed an immune response (e.g., *Escherichia coli, Salmonella, Helicobacter pylori, Staphylococcus aureus, Streptococcal* spp., or *Campylobacter* spp.), or a vaccine with which the subject has been inoculated against (e.g., chickenpox (i.e., varicella-zoster virus (VZV)), polio, German measles (Rubella spp.), mumps, yellow fever, smallpox, Diphtheria, or tetanus (i.e., *Clostridium tetani*)).

It would be understood that a combination or mixture of antigenic peptides (e.g., a "cocktail" of antigenic peptides) can be used to activate a plurality of different antigen-specific T cells (i.e., T cells specific to a plurality of antigens) within a subject, thereby increasing the likelihood and potency of the resulting immune response. For example, a composition used in the peptide alarm therapy described herein can include at least two antigenic peptides (e.g., at least five antigenic peptides, at least ten antigenic peptides, at least twenty antigenic peptides, or more). Notably, the methods described herein require nothing more than one or more antigenic peptides to stimulate the immune system, i.e., no microbial products or other adjuvants, including alum or Toll-like receptor agonists, are required.

A composition used in the peptide alarm therapy described herein can include multiple antigenic peptides from a multitude of microorganisms (e.g., two different viruses, a virus and a bacteria, etc.). For example, such a composition can include at least two antigenic peptides (e.g., at least three antigenic peptides, at least four antigenic peptides, etc.) from at least two microorganisms (e.g., at least three microorganisms, at least four microorganisms, at least five microorganisms, etc.). Simply by way of example, in one embodiment, a composition as described herein can include two or three antigenic peptides from each of two or three different microorganisms. For example, a composition as described herein can include three different antigenic peptides from each of EBV, CMV, and influenza.

As used herein, a skilled artisan would understand how to choose or identify relevant peptides. Antigenic peptides from a number of microorganisms (e.g., infectious diseases) are known in the art and commercially available. For example, and without limitation, antigenic peptides can be one or more antigenic peptides from CMV (see, e.g., Cat. No. PM-C-HCMV-1 from JPT Peptide Technologies), EBV (see, e.g., Cat. Nos. PM-EBV-EBNA1, PM-EBV-EBNA2, PM-EBV-EBNA3a, etc. from JPT Peptide Technologies), HPV (see, e.g., Cat. No. PM-HPV16-E6 from JPT Peptide Technologies), Influenza A (e.g., Cat. Nos. PM-INFA-HA-Cal or PM-INFA MP1 from JPT Peptide Technologies), VZV (see, e.g., Cat. No. PM-VZV-gE from JPT Peptide Technologies), and combinations thereof. In addition, methods of screening and identifying antigenic polypeptides also are well known in the art.

In some instances, it may be desirable to determine the major histocompatibility complex (MHC), also known as human leukocyte antigen (HLA), genotype of the subject to ensure that a correct, appropriate or optimized cocktail of antigenic peptides is administered. For example, antigenic peptides can be selected from defined HLA class I-restricted T cell epitopes (e.g., Cat. No. PM-CEF-E-2 from JPT Peptide Technologies). Methods of determining the MHC genotype or phenotype of a subject are known in the art and include, for example, screening blood with a panel of peptides to identify those peptides to which T cells in the blood sample respond; screening blood with a panel of antibodies to identify individual HLA expression, or sequencing the DNA from cells to determine the HLA genotype. See, for example, labcorp.com/help/patient-test-info/hla-testing on the World Wide Web). T cell response to a particular peptide can be determined using any number of methods including, without limitation, MHC-based class I staining or cytokine (e.g., interferon-gamma) production.

Simply by way of example, Table 1 provides a representative list of anti-viral peptides that would bind to the indicated human MHC I proteins, and also provides the estimated MHC I distribution in the indicated race (W=White, B=Black, H=Hispanic, A=Asian). It would be understood that Table 1 does not include all HLAs, and is intended only to serve as an example.

TABLE 1

Representative Antiviral Peptides

| HLA | Peptide (SEQ ID NO) | Virus of origin | W | B | H | A |
|---|---|---|---|---|---|---|
| A02:01 | CLGGLLTMV (4) | EBV | 46 | 44 | 37 | 18 |
| | GLCTLVAML (3) | EBV | | | | |
| | NLVPMVATV (5) | CMV | | | | |
| | GILGFVFTL (6) | Flu | | | | |
| C07:02 | FRCPRRFCF (7) | CMV | 18 | 18 | 24 | 33 |
| | CRVLCCYVL (8) | CMV | | | | |
| A24:02 | DYCNVLNKEF (9) | EBV | 12 | NA | 25 | 34 |
| | LYTSRMVTNL (10) | CMV | | | | |
| | LYPRPPGSGL (11) | CMV | | | | |
| C04:01 | QYDPVAALF (12) | CMV | 21 | 29 | 26 | 14 |
| A01:01 | VTEHDTLLY | CMV | 27 | 10 | 12 | NA |
| | RGDPFDKNY | CMV | | | | |
| | VSDGGPNLY | Flu | | | | |
| A11:01 | IVTDFSVIK | EBV | 15 | NA | 11 | 38 |
| | ATIGTAMYK | EBV | | | | |
| B07:02 | RPPIFIRRL | EBV | 18 | 16 | 13 | NA |
| | KARDHLAVL | CMV | | | | |
| | NVRRSWEEL | CMV | | | | |
| | TPRVTGGGAM | CMV | | | | |
| | LPFDRTTVM | Flu | | | | |
| A03:01 | RVRAYTYSK | EBV | 24 | 29 | 14 | NA |
| | TLLNCAVTK | CMV | | | | |
| | TVRSHCVSK | CMV | | | | |
| | ILRGSVAHK | Flu | | | | |

W = White, B = Black, H = Hispanic, A = Asian.
The # under W, B, H and A indicate the % of that race expressing the indicated HLA;
NA, not available.
EBV = Epstein-Barr Virus;
CMV = human cytomegalovirus;
Flu = influenza virus.

Many people share at least one HLA/MHC I, and some HLAs are quite common throughout the world's population (e.g., based on race and/or ethnicity). Based on this, the peptides within a composition for use in the peptide alarm therapy described herein can be formulated in a number of different ways.

In some embodiment, a peptide composition can be generated that contains peptides covering the majority of HLA types and could be administered to any subject, irrespective of race and/or HLA type. In such an embodiment, the number of peptides contained within the composition may be higher than the number previously disclosed herein (e.g., considerably higher, e.g., at least 50 antigenic peptides, at least 100 antigenic peptides, between 100 and 200 antigenic peptides, at least 200 antigenic peptides) to ensure that each subject receiving such a universal peptide composition undergoes peptide alarm therapy.

In some embodiments, a peptide composition can be generated that contains peptides covering the majority of HLA types for each race (e.g., based on the common HLA characteristics of that race (see, e.g., Table 1)). As would be expected with the universal peptide composition described above, each peptide within such a generic peptide composition (e.g., in this case, generic to race) may not trigger a response in all subjects, but it would be expected that there would be enough peptides in the composition to ensure that each subject receiving such a generic peptide composition undergoes peptide alarm therapy.

In some embodiments, a product can be formulated that is specific to each HLA. There are many different genes for HLAs, and an individual can express up to six different MHC I proteins at the same time. It is understood that it is this complexity that makes organ transplantation difficult, but it can be used as described herein to specifically customize the peptide compositions used in peptide alarm therapy. In the context of the present disclosure, and simply by way of example, if a subject were determined to have a MHC genotype of A02+, A03+ and B07+, then they could be administered any or all of the 13 peptides shown in Table 1 that are associated with those HLAs.

Peptides can be obtained (e.g., purified) from natural sources (e.g., a biological sample) by known methods such as DEAE ion exchange, gel filtration, and hydroxyapatite chromatography. A peptide also can be obtained, for example, by expressing a nucleic acid in an expression vector. In addition, a peptide can be obtained by chemical synthesis. The term "purified" as used herein with respect to a peptide refers to a peptide that has been separated or purified from cellular components that naturally accompany it. Typically, the peptide is considered "purified" when it is at least 70% (e.g., at least 75%, 80%, 85%, 90%, 95%, or 99%) by dry weight, free from the proteins and naturally occurring molecules with which it is naturally associated. Since a peptide that is chemically synthesized is, by nature, separated from the components that naturally accompany it, a synthetic peptide is "purified." The extent of purity of a peptide can be measured using any appropriate method, e.g., column chromatography, polyacrylamide gel electrophoresis, or HPLC analysis.

The peptides within a composition for use in the peptide alarm therapy described herein can be present individually or, alternatively, the desired combination of peptides can be expressed as a single polypeptides (e.g., containing linker sequences between each of the individual peptides). It would be appreciated that, in certain circumstances, the linker sequences can be designed to be cleaved (e.g., enzymatically, by exposure to light or another physical parameter (e.g., pH, temperature), or by self-cleavage) prior to administration to a subject (e.g., in vitro) or after administration to a subject (e.g., in vivo).

A composition that includes at least one antigenic peptide is typically formulated to be compatible with its intended route of administration. Suitable routes of administration include, for example, oral, topical, and parenteral administration (e.g., intravenous, intramuscular, intraperitoneal, or intratumoral administration).

Compositions for parenteral administration (e.g., intratumoral administration) can be formulated for injection. Such formulations are usually sterile and, can be provided in unit dosage forms, e.g., in ampoules, syringes, injection pens, or in multi-dose containers, the latter usually containing a preservative. The formulations may take such forms as suspensions, solutions, or emulsions in oily or aqueous vehicles, and may contain other agents, such as buffers, tonicity agents, viscosity enhancing agents, surfactants, suspending and dispersing agents, antioxidants, biocompatible polymers, chelating agents, and preservatives. Polymers such as poly(lactic acid), poly(glycolic acid), or copolymers thereof, can serve as controlled or sustained release matrices, in addition to others including, without limitation, PLGA and emulsions.

Pharmaceutically acceptable carriers for delivering compositions are well known in the art. See, for example *Remington: The Science and Practice of Pharmacy*, University of the Sciences in Philadelphia, Ed., 21$^{st}$ Edition, 2005, Lippincott Williams & Wilkins; and *The Pharmacological Basis of Therapeutics*, Goodman and Gilman, Eds., 12th Ed., 2001, McGraw-Hill Co.

The regimen for administering the composition of antigenic peptides and the effective amount(s) of the one or more antigenic peptides contained within such a composition depends upon a variety of factors including the dosage and dosage interval, the sex, age and weight of the subject being treated, the size and aggressiveness of the cancer (e.g., the solid tumor), and the judgment of the subject's physician.

The immunotherapy can be administered concurrently with the administration of the composition comprising the at least one antigenic peptide, or the two forms of therapy can be administered sequentially (e.g., the immunotherapy followed by the peptide alarm therapy or the peptide alarm therapy followed by the immunotherapy). Sequential administration of the therapies can occur within minutes, hours, days or weeks of each other. In addition, each type of therapy can be administered to a subject more than once to achieve the desired results.

The methods described herein (e.g., administration of the immunotherapy and the composition comprising the at least one antigenic peptide (e.g., the peptide alarm therapy composition)) can result in the "treatment" of cancer, specifically the "treatment" of solid tumors. As used herein, the term "treatment" refers to slowing, ameliorating, arresting or reducing the development (e.g., growth, e.g., size) of a solid tumor or at least one of the clinical symptoms resulting thereof.

As reported herein, injection of an antiviral antigenic peptide composition once or twice within a 48 hr period of time directly into a tumor in mice resulted in arrested tumor growth.

Following administration of the immunotherapy and the composition comprising the at least one antigenic peptide (e.g., the peptide alarm therapy composition), the subject can be monitored for a number of responses that are indicative of therapeutic efficacy and/or benefit (e.g., treatment of the solid tumor). For example, a subject can be monitored for at least one of the following (e.g., at least two of the following, at least three of the following): (a) size or volume or density of the solid tumor; (b) presence and/or amount of one or more chemokines (e.g., CXCL9, CXCL10, fractalkine, CCL2, CCL3/4, CCL5); (c) presence and/or amount of leukocytes (e.g., inflammatory monocytes, B cells); (d) presence and/or amount of serum antibodies; (e) presence and/or amount of an immunotherapeutic (e.g., CAR-T cells) associated with or in the vicinity of the solid tumor; (0 activation of local dendritic cells; (g) activation of NK cells; and/or (h) up-regulation of vascular adhesion molecules (e.g., VCAM-1).

The antigenic peptide composition described herein can be provided in an article of manufacture, or the antigenic peptide composition can be directly incorporated into oncolytic therapy (e.g., the FDA-approved Imlygic recombinant oncolytic virus (Amgen) or another virus that produces antiviral proteins) to express antiviral peptides in the tumor. Simply by way of example, an article of manufacture can include a saline solution containing, for example, 4-6 different peptides of about 8 to about 10 amino acids in length that are tailored to specific HLA types. In instances in which common or well-characterized HLAs are lacking (e.g., common pathogen epitopes are unknown), an article of manufacture can contain from about 50 different peptides up to about 200 different peptides derived from common human pathogens that are each about 10 to about 20 amino acids in length.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A: Synergy Between Peptide Alarm Therapy and Checkpoint Inhibitor
Immunotherapy Example 1—Materials and Methods Adult C57B/6 mice were given $5\times10^5$ naïve OTI CD8 T cells i.v., which bear a T cell receptor specific for the SIINFEKL (SEQ ID NO:1) peptide of chicken ovalbumin (ova) presented in the Kb MHC I molecule. The next day, all animals were infected i.v. with $1\times10^6$ pfu of recombinant vesicular stomatitis virus producing chicken ovalbumin (VSV-ova). This induces memory OTI CD8 T cells. 32-45 days later, $1\times10^5$ B16 melanoma cells were injected subcutaneously or, in some instances, $2.5\times10^5$ TBL12 leukemia cells were injected intradermally. Tumor size was monitored daily with calipers.

Peptide injections were performed directly into the established tumor. 0.5 µg peptide in 30 µl PBS was injected into the tumor either once or twice (2 days apart), as noted. KAVYNFATM (SEQ ID NO:2) peptide was used as irrelevant control peptide, which is from the glucoprotein of lymphocytic choriomeningitis virus (LCMV). SIINFEKL (SEQ ID NO:1) peptide was used to stimulate the memory OTI CD8 T cells.

CAR T cells were generated by transduction of a chimeric antigen receptor specific for human CD19 along with signaling domains from CD28 and 41BB. These were also positive for the Thy 1.1 marker. $5\times10^6$ CAR T cells were infused intravenously into animals.

The number of Thy 1.1+ CAR T cells in the tumor were enumerated by flow cytometry after enzymatic digestion of the tumor with DNAse and collagenase, followed by Ficoll density centrifugation.

Example 2—Preliminary Results

The experiments described in Example 1 demonstrate that peptide activation of previously established microbe-specific memory CD8 T cells using only cognate peptide in PBS can result in significant inhibition of a rapidly growing tumor, even when the tumor has already been established and palpable. See FIG. 1. These T cells have no antigenic overlap with the tumor, yet their activation results in a change from an immune-suppressive environment to an immune-stimulatory one, without the need for adjuvant/s. Because the peptide was injected directly into the tumor, this is evidence that these viral-specific CD8 T cells (OTI, which refers to OVA T cells MHC I, i.e., CD8 T cells specific for SIINFEKL (SEQ ID NO:1) that were induced to form a broadly distributed memory population due to infection of the mouse with vesicular stomatitis virus-Ova) are present and functional in tumors.

Figure 2:
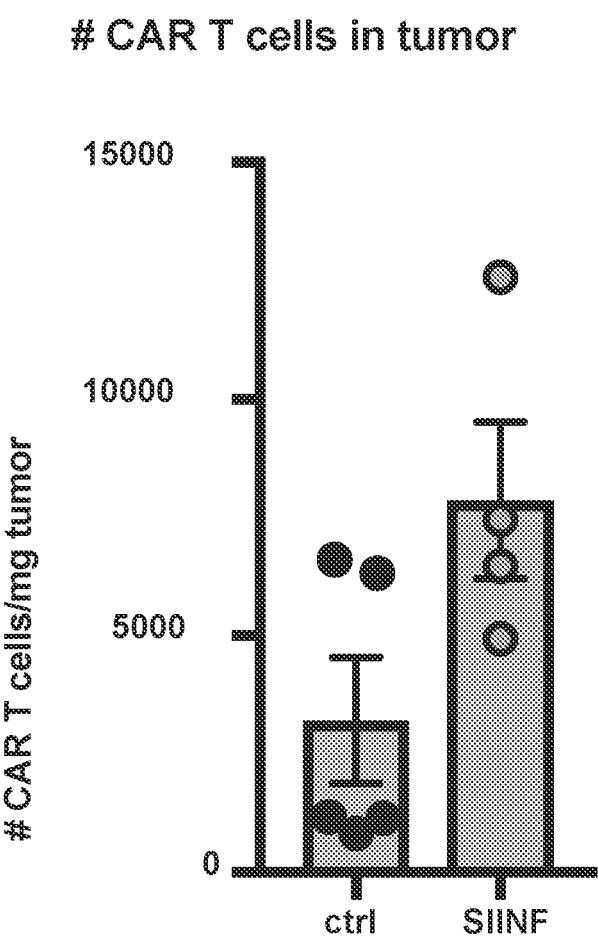
FIG. 2 is data showing adult C57B/6 mice that were given naïve OTI CD8 T cells, which are specific for the SIINFEKL (SEQ ID NO:1) peptide of chicken ovalbumin (ova). The next day, all animals were infected iv with a recombinant vesicular stomatitis virus producing chicken ovalbumin (VSV-ova). This induces memory OTI CD8 T cells that are broadly distributed throughout the body. 32-45 days later, $2.5 \times 10^5$ TBL12 tumor cells were injected intradermally. 7 days later, $5 \times 10^6$ CAR T cells specific for human CD19 were injected iv. Three hours later, 0.5 µg peptide in 30 µl PBS was injected into the tumor once. Either irrelevant or control peptide (black) was injected or SIINFEKL (SEQ ID NO:1) peptide was injected to stimulate OTI memory T cells (red). The number of CAR T cells were enumerated in tumor 48 hours after peptide injection.

The use of peptide to activate microbe-specific memory T cells present in tumors also can synergize with other types of cancer immunotherapy such as adoptive cell transfer of CART cells or checkpoint blockade inhibitors. The experiments described in this document show that only one peptide injection into tumors results in more CAR T cell migration into the tumor environment. See FIG. 2. Thus, CAR T cell therapy of tumors can be significantly improved when used in combination with the peptide activation of microbe-specific memory CD8 T cells described herein.

Example 3—Mice

C57BL/6J (B6) female mice were purchased from The Jackson Laboratory (Bar Harbor, Me.). CD90.1+ OT-I and CD45.1+ OT-I mice were fully backcrossed to C57BL/6J mice and maintained in an animal colony. All mice used in experiments were 5-14 weeks of age.

Example 4—Adoptive Transfers and Infections

Antiviral OT-I immune chimeras were generated by transferring $5\times10^4$ CD90.1 or CD45.1 OT-I CD8+ T cells from female mice into naive 6-8 week old C57BL/6J female mice, and then infecting those mice with $1\times10^6$ PFU of vesicular stomatitis virus expressing chicken ovalbumin (VSVova) i.v.

Example 5—Tumor Induction, In Vivo Peptide Delivery, and In Vivo Antibody Treatment 150,000 B16 cells were injected s.c. into the right flank (or left flank if a re-challenge experiment). For local tumor T cell reactivation experiments involving peptides, 0.5 µg of the indicated peptides (New England Peptides) were delivered by direct intratumor injection in a volume of 30 µl. Anti-PD-L1 (clone B7-H1, Bioxcel) was injected i.v. at 0.2 mg/mouse every other day for a total of three times starting at the time of first intratumoral peptide injection. The peptides used in the mouse studies were KAVYNFATM (gp33; SEQ ID NO:2) from LCMV (control) and SIINFEKL (SEQ ID NO:1) from ovalbumin.

Example 6—Experimental Results

Figure 3:
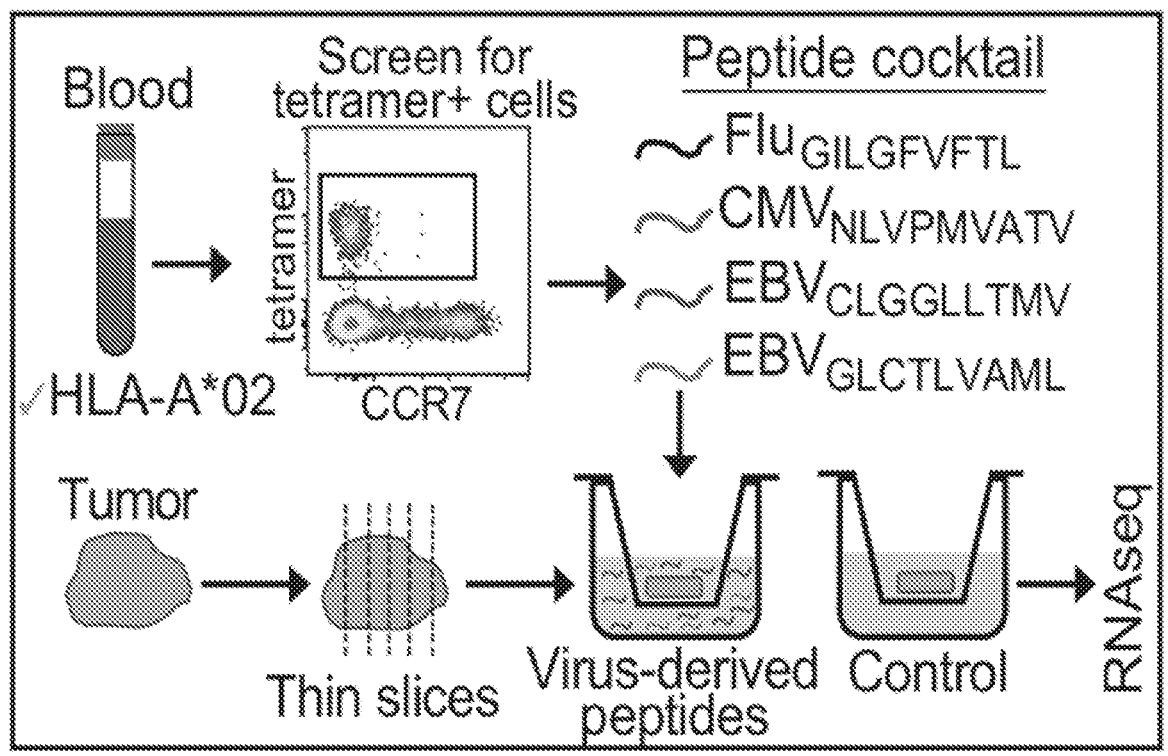
FIG. 3 is a schematic showing test peptide alarm therapy in human tumor explants. Tetramer staining of blood will inform which peptides to use. Human tumor explants are treated with appropriate viral peptides (SEQ ID NOs: 6, 5, 4 and 3 (top to bottom)) and analyzed by RNAseq 9 h later or flow cytometry 24 h later.
Figure 4:
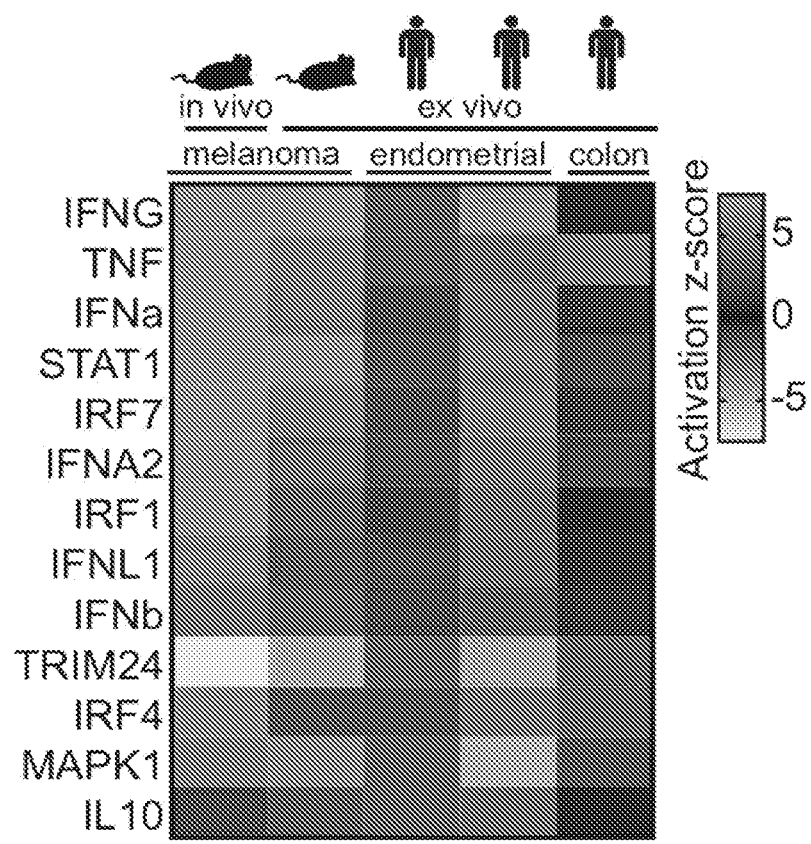
FIG. 4 shows that peptide alarm therapy of human tumors induces immune activation. IPA analysis of differentially expressed genes reveals highly similar patterns of upstream regulators in in vivo mouse tumors, mouse tumor explants, and human tumor explant after peptide alarm therapy. Mice with established B16 melanoma tumors were given antiviral peptide intra-tumorally (left column). Established B16 melanoma tumors in mice were excised and used as explants to test as in FIG. 3 (left middle column). Two endometrial tumors and one colon tumor from humans were used in vitro for explants as in FIG. 3. After peptide treatment, tumor cells were harvested and sent for RNA sequencing analysis. This IPA analysis occurred using these data.

Ex vivo stimulation assay of tumor explants was used to test in situ reactivity of antiviral T cells in tumors using viral peptides. A schematic of the process is shown in FIG. 3. Mice with antiviral memory CD8 T cells were injected with B16 melanoma cells s.c. When the tumor was palpable, peptide was injected into the tumor and 12 h later, tumor was isolated and prepared for RNA sequencing (FIG. 4, first column). In another cohort of mice, tumor was excised when palpable and prepared, as described for FIG. 3, for ex vivo culture with peptides (FIG. 7, second column). Two endometrial tumors and one colon tumor from humans were used in vitro for explants, as shown in FIG. 3. After 9 h of peptide treatment in vitro, tumor cells were harvested and sent for RNA sequencing (FIG. 4, third, fourth and fifth columns). These experiments demonstrated that peptide alarm therapy induced immune activation.

Figure 5A:
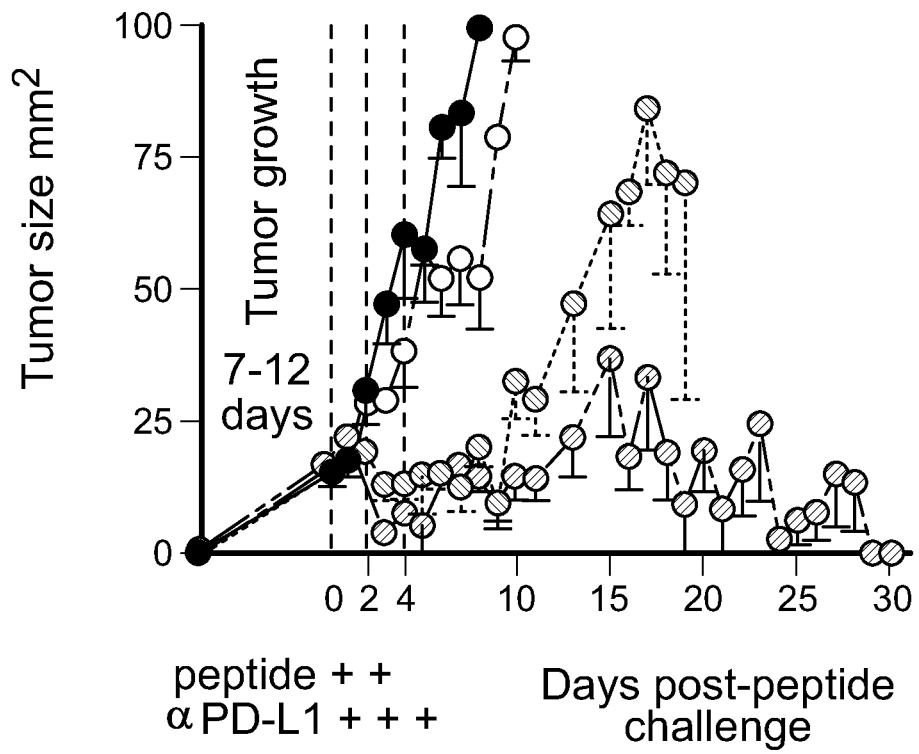
FIG. 5A shows tumor size and FIG. 5B shows the survival of mice with palpable B16 tumors that were treated twice with reactivating SIINFEKL (SEQ ID NO:1) viral (or control) peptide+/−anti-PDL1 checkpoint blockade.
Figure 5B:
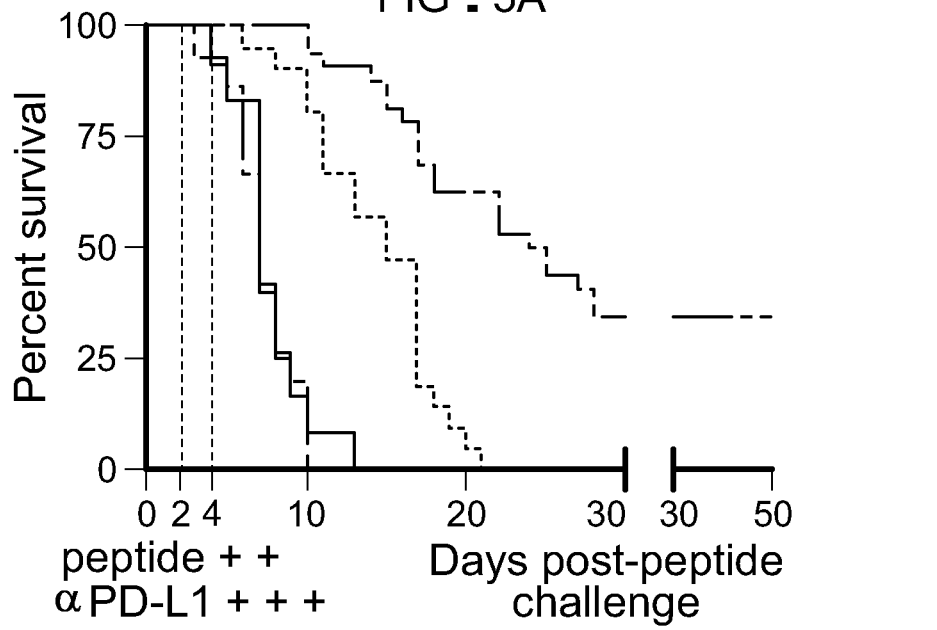

Mice with antiviral memory CD8 T cells were injected with B16 melanoma cells s.c. When a tumor was palpable, peptides were injected twice into the tumor over 48 h. Some mice also received three injections of checkpoint blockade anti-PDL1 antibody i.v. FIG. 5A shows the tumor size and FIG. 5B shows the survival of mice following injection of an irrelevant peptide (black, green), the viral peptide (red, blue), and the viral peptide with the checkpoint blockade anti-PDL1 antibody (green, blue).

These results demonstrate that peptide alarm therapy arrests tumor growth and is synergistic with PD-L1 blockade (FIG. 5). Blocking PD-L1/PD-1 interactions with an injected antibody (which is a FDA-approved approach to treat humans with cancer) is ineffective against mouse B16 melanoma, while peptide therapy is more effective. If blocking PD-L1/PD-1 interactions is combined with peptide therapy, some mice were cured of their B16 melanoma. Accordingly, peptide therapy has efficacy all by itself, but peptide therapy also extends the scope of effectiveness of PD-L1/PD-1 targeted therapy.

Figure 6:
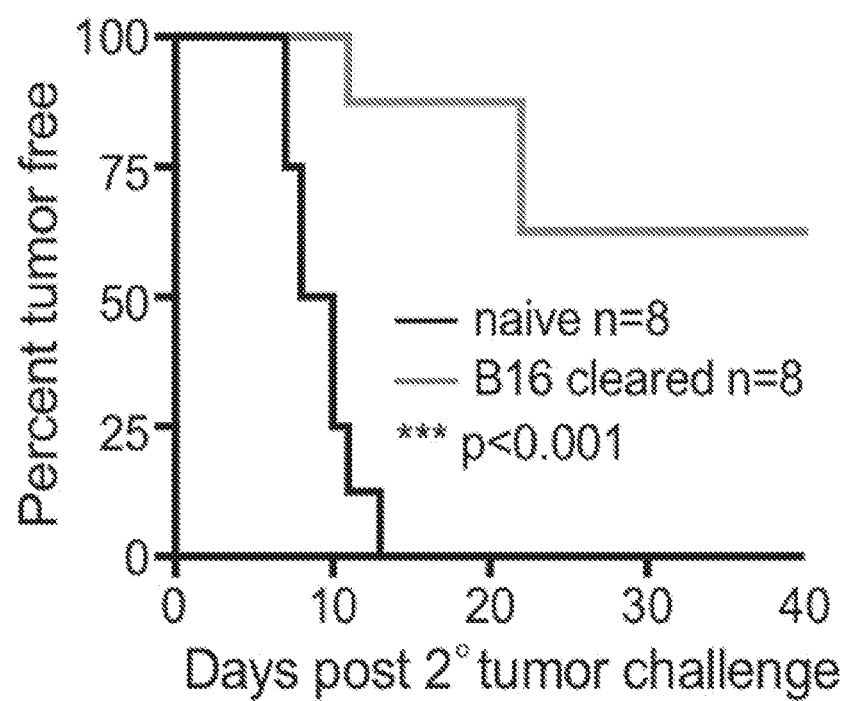
FIG. 6 shows that mice cured of B16 are resistant to secondary tumor challenge. Cured mice (FIG. 5) were re-challenged with B16 on the opposite flank >5 weeks later in the absence any of additional treatment.

The mice that were treated with viral peptide and PD-L1 blockade from FIG. 5 (blue line) were tested for antitumor immunity. At least 5 weeks after initial B16 tumor was cleared, B16 cells were injected s.c. in the opposite flank. FIG. 6 shows the percent of naïve control or cured peptide+ anti-PD-L1 treated mice that remained tumor-free after B16 re-challenge.

Mice cured with PD-L1/PD-1 blockade and peptide therapy can attack the tumor anywhere throughout the body, even if the tumor appears months later at a different location. Significantly, There was no need for sustained therapy to get this effect. Thus, antiviral T cell reactivation promotes tumor clearance and induces long-lasting, systemic tumor immunity.

Part B: The Presence of Antiviral CD8 T Cells in Human Blood and Tumors

Figure 7A:
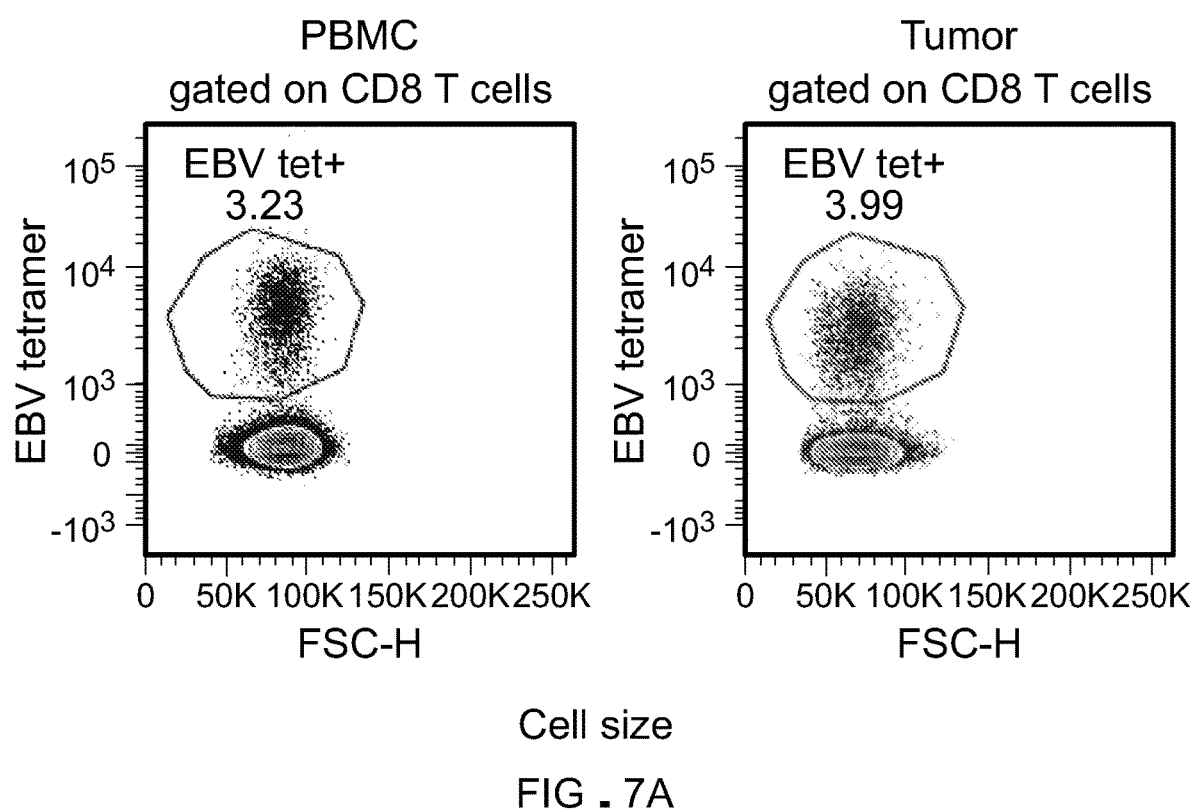
FIG. 7 are graphs showing that Epstein-Barr virus-specific CD8 T cells of diverse phenotypes populate human endometrial tumors. Peripheral blood mononuclear cells (PBMC) and endometrial tumor were isolated from the same patient. Blood was subjected to Ficoll density gradient centrifugation to isolate PBMCs. Tumor was enzymatically digested and then subjected to density gradient centrifugation to isolate lymphocytes. MHC I tetramers complexing HLA-A*0201 with the Epstein-Barr virus (EBV) epitope (GLCTLVAML; SEQ ID NO:3) from the lytic cycle protein, BMLF1, identified CD8 T cells specific for this EBV epitope via flow cytometry (FIG. 7A). CD69 and CD103 expression on gated EBV tetramer+ CD8 T cells are shown in FIG. 7B.
Figure 7B:
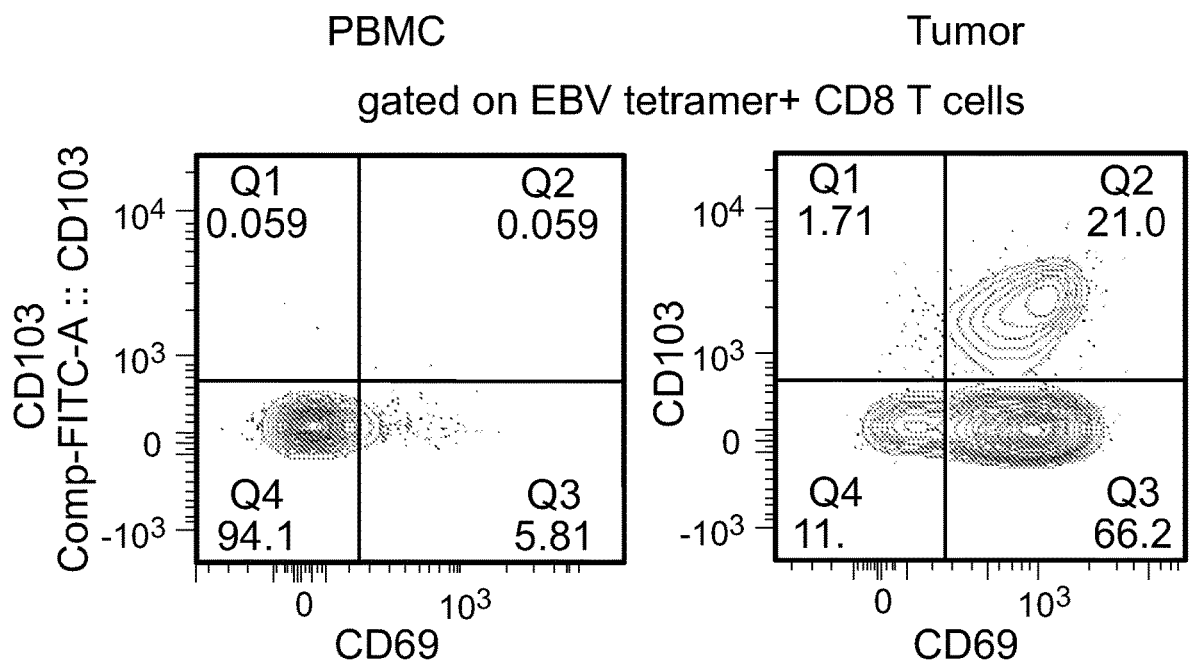

Example 7—Epstein-Barr Virus-Specific CD8 T Cells of Diverse Phenotypes Populate Human Endometrial Tumors Peripheral blood mononuclear cells (PBMC) and endometrial tumor were isolated from the same patient. Blood was subjected to Ficoll density gradient centrifugation to isolate PBMCs. Tumor was enzymatically digested and then subjected to density gradient centrifugation to isolate lymphocytes. MHC I tetramers complexing HLA-A*0201 with the Epstein-Barr virus (EBV) epitope, GLCTLVAML (SEQ ID NO:3), from the lytic cycle protein, BMLF1, identified CD8 T cells specific for this EBV epitope via flow cytometry are shown in FIG. 7A. CD69 and CD103 expression on gated EBV tetramer+ CD8 T cells is shown in FIG. 7B.

Example 8—Procurement and Processing of Human Blood and Tissue Samples

All tumor tissue and blood were obtained from male or female patients age 16-80 undergoing routine surgical resection of solid tumors or tumor metastases. Tumor tissue not required for pathological diagnostic procedures was obtained after surgical resection at the University of Minnesota and collected and de-identified by the Tissue Procurement Facility (BioNet, University of Minnesota). Informed consent was obtained from all subjects. The University of Minnesota Institutional Review Board approved all protocols used. Blood was collected in EDTA collection tubes and tumors were collected in RPMI media containing 5% FBS. All samples were stored at 4 degrees until processed (within 24 hours). Specimens reported on were obtained from HLA*A02+ patients that had sufficient tetramer+ cells for analysis by flow cytometry. Human blood was processed by Ficoll gradient. Tumors were minced and digested in Collagenase type IV (endometrial) or Collagenase Type I (all others). They were then dissociated via gentleMACS Dissociator 1× (glioblastoma or brain metastases) or 2× (all others) and lymphocytes purified on a 44/67% Percoll (GE Healthcare) gradient. The following peptides were used in human studies: CLGGLLTMV ($EBV_{CLG}$) (SEQ ID NO:4), GLCTLVAML ($EBV_{GLC}$) (SEQ ID NO:3), NLVPMVATV ($CMV_{NLV}$) (SEQ ID NO:5), or GILGFVFTL ($Flu_{GIL}$) (SEQ ID NO:6).

Example 9—Transwell Cultures and RNA Isolation

Tumors were sliced into thin sections manually with a sharp surgical blade. Sections were then incubated in media on 24-well polycarbonate transwell inserts with a 0.4 μm pore size (Corning) and maintained in 5% $CO_2$ and atmospheric oxygen levels (Davies et al., 2015, Sci. Reports, 5:17187). Tissues were incubated with viral peptides at 10 μg/mL or in equal volume of DMSO for 9 hours. Tumor sections were stored in RNAlater (ThermoFisher) at 4° C. overnight, then stored at −80° C. until further processing. For RNA isolation, tissue was thawed on ice in 1 mL TRIZOL (Invitrogen) then homogenized with a Tissue Tearor homogenizer, BioSpec. RNA was then isolated following the TRIZOL recommended protocol. Resulting RNA was then further purified using Qiagen RNA Cleanup Kit.

Figure 8:
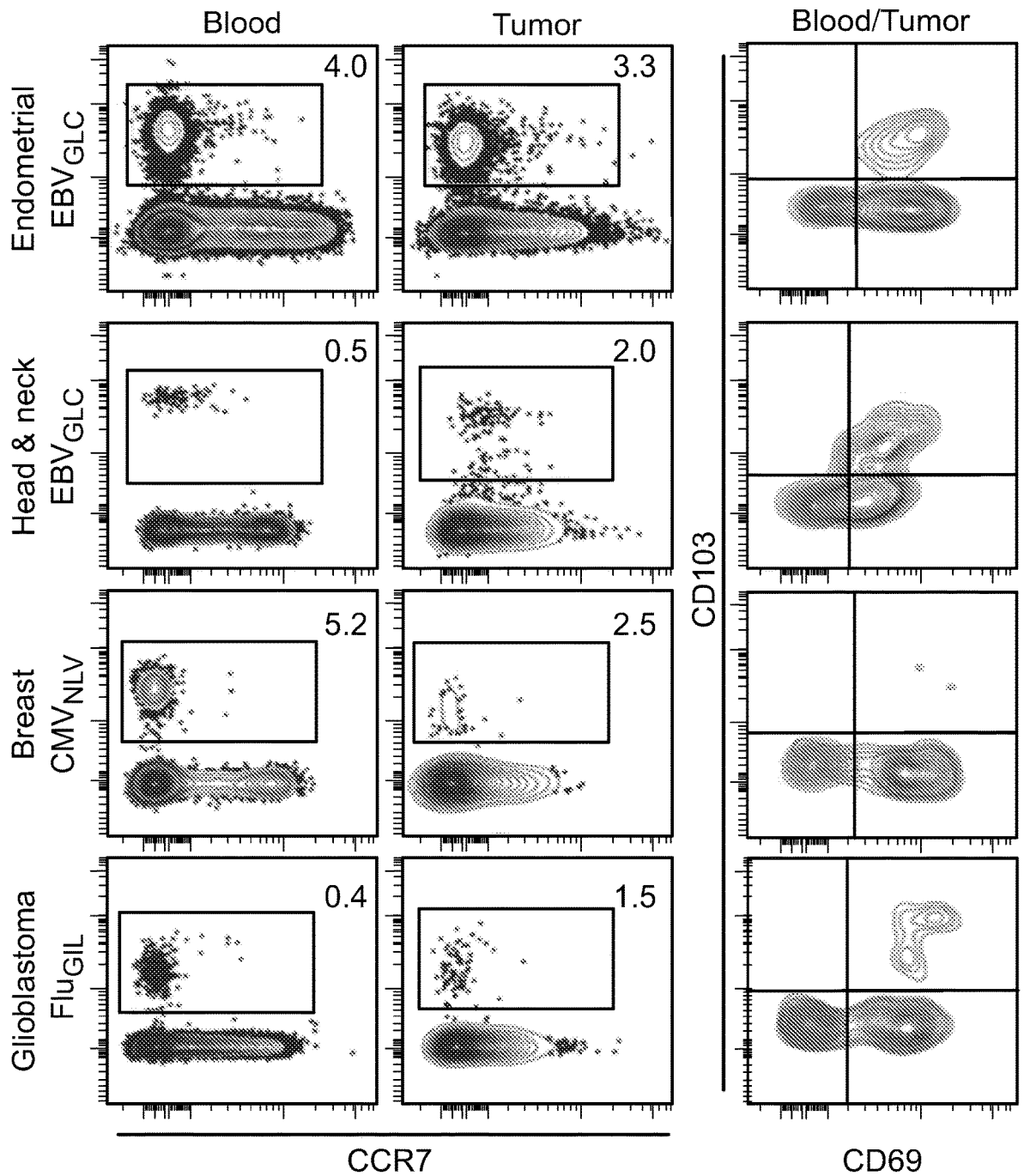
FIG. 8 shows that virus-specific CD8+ T cells populate human tumors and have a TRM phenotype. Tetramer staining for EBV, CMV or Flu-specific CD8+ T cell populations in HLA-A*02+human tumors and paired blood. Gated on CD8+/CD3+ cells. Right column; CD69 and CD103 TRM phenotype of tetramer-positive cells.

Example 10—RNA Library Preparation and Sequencing mRNA libraries were generated using the TruSeq Stranded mRNA Library Prep kit (Illumina) and sequenced on an Illumina HiSeq 2500 in 50-base paired-end reactions. Fastq files were verified for quality control using the fastqc software package. Low-quality segments and adapters were trimmed using Trimmomatic. Quality-filtered reads were aligned to either the mouse genome GRCm38 or the human genome GRCh38 using Hisat2 (Kim et al., 2015, Nat. Methods, 12:357-60). Differentially expressed genes were determined using the DESeq2 R package (Love et al., 2014, Genome Biol., 15:550) where false-discovery rate (FDR) <0.1 was considered significant. Upstream transcriptional regulators were generated through the use of IPA (QIAGEN Example 11—Experimental Results As described herein, blood and tumor samples were obtained from the same HLA-A*02+ patient, and lymphocytes were isolated from tumor and blood and stained with HLA-A*02+ tetramers to detect EBV, CMV or Flu-specific CD8+ T cells. FIG. 8 shows tetramer staining to detect the indicated virus-specific CD8 T cells in a patient's blood and tumor (left) and the phenotype of these T cells in blood and tumor (right). Results from these experiments demonstrated that antiviral CD8 T cells are present in human blood and tumors (FIG. 8).

Figure 9:
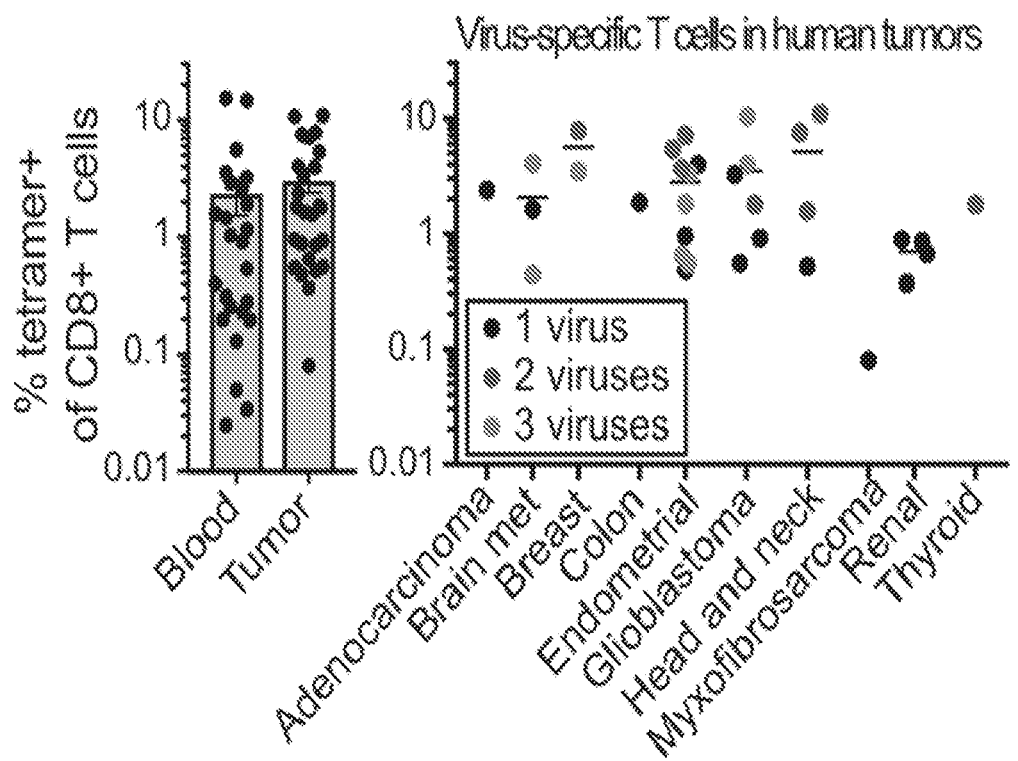
FIG. 9 shows that virus-specific T cells are more frequent in human tumors than blood. Sum of the frequencies of all four tetramers in blood and all tumors combined (left graph), and stratified by tumor type (right graph). The number of viruses a patient had detectable tetramer+ cells for is denoted by color where black=1 virus, blue=2 viruses and red=3 viruses.

Also as described herein, lymphocytes were isolated from tumor and blood, and stained with HLA-A*02+ tetramers to detect EBV, CMV or Flu-specific CD8+ T cells. Thirty-three tumor/blood samples were analyzed, spanning ten different tumor types. FIG. 9 shows the percent of antiviral CD8 T cells in paired blood and tumors samples from multiple patients (left) and whether individual patients had CD8 T cells specific for one, two or three viruses in their tumor (right). Therefore, these experiments demonstrated that antiviral CD8 T cells are numerous in human tumors (FIG. 9).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of treating a solid tumor in a human subject, comprising administering immunotherapy to the subject and administering a composition comprising at least two antigenic peptides to the solid tumor, wherein the composition comprises FRCPRRFCF (SEQ ID NO:7) and CRVLCCYVL (SEQ ID NO:8) or DYCNVLNKEF (SEQ ID NO: 9), LYTSRMVTNL (SEQ ID NO: 10) and LYPRPPGSGL (SEQ ID NO: 11) wherein administering the composition to the solid tumor results in activation of resident memory T cells.

2. The method of claim 1, wherein the immunotherapy is selected from the group consisting of CAR T cells, monoclonal antibodies, checkpoint blockade inhibitors, and personalized vaccines.

3. The method of claim 1, wherein the composition comprises at least one additional antigenic peptide from a further virus or a bacteria.

4. The method of claim 3, wherein the further virus is selected from the group consisting of an influenza virus, a cold virus, an adenovirus, an adeno-associated virus, a cytomegalovirus (CMV), a measles virus (e.g., rubeola), an Epstein-Barr virus, human papillomavirus (HPV), a norovirus, a polyoma virus, a hepatitis A, B and/or C virus, a Zika virus, a respiratory syncytial virus (RSV), and a herpes simplex virus (HSV).

5. The method of claim 3, wherein the further bacteria is selected from the group consisting of *Escherichia coli, Salmonella, Helicobacter pylori, Staphylococcus aureus, Streptococcal spp.*, and *Campylobacter spp.*

6. The method of claim 1, wherein at least one of the at least two antigenic peptides is from a vaccine.

7. The method of claim 1, wherein the composition comprising at least two antigenic peptides is administered to the solid tumor via injection.

8. The method of claim 1, wherein the composition comprising at least two antigenic peptides is administered to the solid tumor a plurality of times.

9. The method of claim 1, further comprising determining the major histocompatibility complex (MHC)/Human Leukocyte Antigen (HLA) genotype of the subject.

10. The method of claim 1, further comprising monitoring at least one of the following or at least two of the following or at least three of the following:
- size of the solid tumor;
- presence and/or amount of one or more chemokines;
- presence and/or amount of leukocytes;
- presence and/or amount of serum antibodies;
- presence and/or amount of an immunotherapeutic associated with or in the vicinity of the solid tumor;
- activation of local dendritic cells;
- activation of NK cells; and/or
- up-regulation of vascular adhesion molecules.

11. The method of claim 1, wherein the solid tumor is selected from the group consisting of glioblastoma, colon cancer, melanoma, breast cancer, pancreatic cancer, head and neck cancer, and retinoblastoma.

12. The method of claim 1, wherein the resident memory T cells are microbe-specific resident memory T cells.

13. The method of claim 12, wherein the microbe-specific resident memory T cells are non-lymphoid, microbe-specific resident memory T cells.

\* \* \* \* \*

UNITED STATES PATENT AND TRADEMARK OFFICE
CERTIFICATE OF CORRECTION

PATENT NO. : 12,370,256 B2
APPLICATION NO. : 16/635205
DATED : July 29, 2025
INVENTOR(S) : David B. Masopust, Jr. and Vaiva D. Vezys Page 1 of 1

It is certified that error appears in the above-identified patent and that said Letters Patent is hereby corrected as shown below:

In the Claims

Column 24, Line 52, i.e., Line 3 in Claim 9, change "virus (e.g., rubeola)," to --virus,--.

Signed and Sealed this
Thirtieth Day of September, 2025

John A. Squires
*Director of the United States Patent and Trademark Office*